US011123034B2

United States Patent
Schaefer et al.

(10) Patent No.: US 11,123,034 B2
(45) Date of Patent: Sep. 21, 2021

(54) SPECTRAL IMAGING (71) Applicant: KONINKLIJKE PHILIPS N.V., Eindhoven (NL)

(72) Inventors: Dirk Schaefer, Hamburg (DE); Axel Thran, Hamburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 13 days.

(21) Appl. No.: 16/663,824

(22) Filed: Oct. 25, 2019

(65) Prior Publication Data
US 2020/0054302 A1    Feb. 20, 2020

Related U.S. Application Data (63) Continuation of application No. 14/378,179, filed as application No. PCT/IB2013/051361 on Feb. 20, 2013, now Pat. No. 10,485,503.

(Continued)

(51) Int. Cl.
*A61B 6/00* (2006.01)
*G01T 1/20* (2006.01)
(Continued)

(52) U.S. Cl.
CPC .......... *A61B 6/5205* (2013.01); *A61B 5/0075* (2013.01); *A61B 6/42* (2013.01); *G01T 1/2008* (2013.01); *G01T 1/2985* (2013.01)

(58) Field of Classification Search
CPC ....... A61B 6/5205; A61B 5/0075; A61B 6/42; G01T 1/2008; G01T 1/2985
See application file for complete search history.

(56) References Cited

U.S. PATENT DOCUMENTS

| 6,343,111 B1 * | 1/2002 | Avinash | A61B 6/482 348/E5.088 |
| 6,683,934 B1 * | 1/2004 | Zhao | A61B 6/032 378/37 |

(Continued)

FOREIGN PATENT DOCUMENTS

| JP | 2009511873 | 3/2009 |
| JP | 2010274108 | 12/2010 |

OTHER PUBLICATIONS

Alvarez, R.E. et al., Energy-Selective Reconstruction X-Ray Computerized Tomography, 1976, Phys. Med. Biol., 21(5)733-744.

*Primary Examiner* — Katherine L Fernandez
*Assistant Examiner* — Colin T. Sakamoto
(74) *Attorney, Agent, or Firm* — Larry Liberchuk (57) ABSTRACT

An imaging system includes radiation source that emits radiation that traverses an examination region and a portion of a subject therein and a detector array that detects radiation that traverses the examination region and the portion of the subject therein and generates a signal indicative thereof. A volume scan parameter recommender recommends at least one spectral scan parameter value for a volume scan of the portion of the subject based on a spectral decomposition of first and second 2D projections acquired by the radiation source and detector array. The first and second 2D projections have different spectral characteristics. A console employs the recommended at least one spectral scan parameter value to perform the volume scan of the portion of the subject.

13 Claims, 4 Drawing Sheets

Related U.S. Application Data (60) Provisional application No. 61/603,596, filed on Feb. 27, 2012.

(51) Int. Cl.
*G01T 1/29* (2006.01)
*A61B 5/00* (2006.01)

(56) References Cited

U.S. PATENT DOCUMENTS

| | | | |
|---|---|---|---|
| 6,917,697 B2 * | 7/2005 | Avinash | A61B 6/00 378/53 |
| 7,826,587 B1 * | 11/2010 | Langan | A61B 6/405 378/16 |
| 8,031,831 B2 * | 10/2011 | Zou | A61B 6/032 378/16 |
| 8,199,874 B2 | 6/2012 | Toth | |
| 8,611,489 B2 | 12/2013 | Roesel | |
| 9,275,189 B2 | 3/2016 | Walker | |
| 2002/0075997 A1 * | 6/2002 | Unger | A61B 6/544 378/98.9 |
| 2002/0186872 A1 * | 12/2002 | Avinash | A61B 6/00 382/132 |
| 2003/0142787 A1 * | 7/2003 | Jabri | A61B 6/4233 378/98.12 |
| 2003/0152258 A1 * | 8/2003 | Jabri | G06T 5/50 382/132 |
| 2003/0169848 A1 * | 9/2003 | Jabri | A61B 6/505 378/98.9 |
| 2004/0101087 A1 | 5/2004 | Hsieh | |
| 2004/0184574 A1 * | 9/2004 | Wu | A61B 6/563 378/5 |
| 2007/0076842 A1 * | 4/2007 | Tkaczyk | A61B 6/4085 378/5 |
| 2007/0189443 A1 * | 8/2007 | Walter | A61B 6/504 378/4 |
| 2008/0253509 A1 * | 10/2008 | Schlomka | G01V 5/0025 378/19 |
| 2012/0045109 A1 * | 2/2012 | Proksa | A61B 6/504 382/131 |

\* cited by examiner

SPECTRAL IMAGING

The following generally relates to spectral imaging and more particularly to determining a suitable tube voltage for a spectral volume scan based on two or more two-dimensional (2D) projection scans (scanograms) performed at two or more different kVps from approximately the same acquisition view, and is described with particular application to computed tomography (CT).

A conventional CT scanner generally includes an x-ray tube mounted on a rotatable gantry, opposite a detector array, across an examination region. The rotatable gantry, and hence the x-ray tube, rotates around the examination region. The x-ray tube emits radiation that traverses the examination region and a portion of a subject therein and is detected by the detector array. The detector array generates and outputs a signal indicative of the scanned portion of a subject. The signal is reconstructed to generate three dimensional volumetric image data indicative of the scanned portion of a subject.

The volumetric image data includes voxels represented in terms of gray scale values corresponding to relative radiodensity. The gray scale values reflect the attenuation characteristics of the scanned subject, and generally show anatomical structures within the scanned subject. Since the absorption of a photon by a material is dependent on the energy of the photon traversing the material, the detected radiation also includes spectral information. However, conventional CT image data does not reflect the spectral information as the signal is proportional to an energy fluence integrated over the energy spectrum.

A spectral CT scanner captures the spectral information, which is indicative of the elemental or material composition (e.g., atomic number) of the material of the scanned portion of the subject. Spectral CT scanner configurations include two or more x-ray tubes angularly offset from each other and configured to emit radiation having different peak emission voltages, a single x-ray tube configured to switch between at least two different kVps (e.g., 80 kVp and 140 kVp), a single broad spectrum x-ray tube and an energy-resolving detectors, and/or a combination thereof.

Volume scans typically are planned (i.e., scan position and scan length) using a 2D projection image from a 2D projection scan at a fixed kVp. However, the 2D projection image generally does not provide sufficient information to optimally select scan parameters such as kVps for a spectral volume scan, and image quality depends on the kVp. For example, good spectral performance can be achieved with a lower value (e.g. 80 kVp) for the lower kVp. However, with a larger subject, fewer 80 kVp photons pass through the subject, and the volumetric image data may be noisy with degraded image quality.

Aspects described herein address the above-referenced problems and others.

In one aspect, an imaging system includes radiation source that emits radiation that traverses an examination region and a portion of a subject therein and a detector array that detects radiation that traverses the examination region and the portion of the subject therein and generates a signal indicative thereof. A volume scan parameter recommender recommends at least one spectral scan parameter value for a volume scan of the portion of the subject based on a spectral decomposition of first and second 2D projections acquired by the radiation source and detector array. The first and second 2D projections have different spectral characteristics. A console employs the recommended at least one spectral scan parameter value to perform the volume scan of the portion of the subject.

In another aspect, a method includes receiving first 2D projection having a first spectral characteristic and receiving second 2D projection having a second spectral characteristic, wherein the first and second spectral characteristics are different. The method further includes spectrally decomposing the first and second data into at least two different components. The method further includes determining a physical characteristic of the scanned subject based on the decomposed data. The method further includes determining at least one spectral scan parameter value for a volume scan of the subject based on the determined physical characteristic. The method further includes performing the volume scan of the subject using the at least one spectral scan parameter value.

In another aspect, a computer readable storage medium is encoded with computer readable instructions. The computer readable instructions, when executed by a processor, cause the processor to acquire several 2D projections at least at two different emission spectrums from at least one acquisition angle and determine at least one spectral scan parameter settings for a volume scan based on the acquired several 2D projections.

The invention may take form in various components and arrangements of components, and in various steps and arrangements of steps. The drawings are only for purposes of illustrating the preferred embodiments and are not to be construed as limiting the invention.

Figure 1:
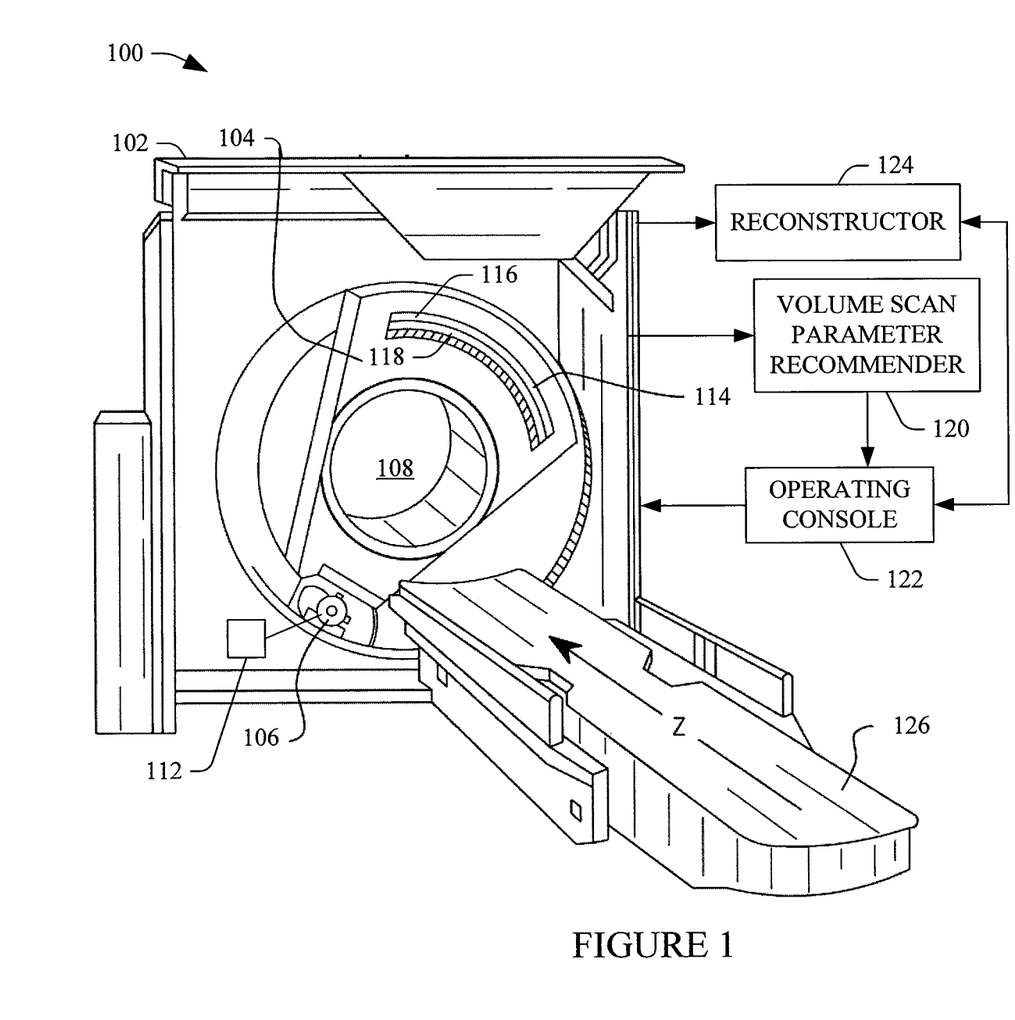
FIG. 1 schematically illustrates an example imaging system in connection with a volume scan parameter recommender.

FIG. 1 schematically illustrates an imaging system 100 such as a computed tomography (CT) scanner 100. The imaging system 100 includes a stationary gantry 102 and a rotating gantry 104. The rotating gantry 104 is rotatably supported by the stationary gantry 102. The rotating gantry 104 is configured to rotate around an examination region 108 about a longitudinal or z-axis.

At least one radiation source 106, such as an x-ray tube, is supported by the rotating gantry 104 and rotates therewith. The rotating gantry 104 rotates to move the radiation source 106 to a predetermined static angular location, if not already at the location, for example, for a 2D projection scan. The rotating gantry 104 also rotates to rotate the radiation source 106 around the examination region 108 for volume scan.

A radiation source voltage determiner 112 is configured to switch the peak emission voltage between two or more voltages (e.g., 80 kVp, 100 kVp, 140 kVp, etc.) for 2D projection and/or volume scans. By way of non-limiting example, for a 2D projection scan, one kVp can be used for an anterior-posterior (AP) projection scan (and/or a lateral scan) in one direction along the z-axis and another kVp can be used for an AP scan (and/or a lateral scan) in the same or an opposing direction along the z-axis.

Alternatively, two different 2D projections at different kVps and at approximately a same acquisition angle can be acquired through fast kV switching and a backward jump of the focal spot. This may facilitate reducing mismatch artifact due to gantry motion. The lower kVp value, generally, is high enough to mitigate photon starvation caused by the absorption of all or substantially all of the photons. The radiation source voltage determiner 112 can also be used to drive the source 106 with a single fixed kVp.

A one or two dimensional radiation sensitive detector array 114 subtends an angular arc opposite the examination region 108 relative to the radiation source 106. The detector array 114 detects radiation that traverses the examination region 108 and generates an output signal indicative thereof. The illustrated detector array 114 includes a photosensor array 116 with photosensors such as photodiodes or the like and a scintillator array 118, which is optically coupled to the photosensor array 116 on a light sensitive side of the photosensor array 116.

The detector array 114 is arranged in the scanner 100 so that the scintillator array 118 receives radiation emitted by the source 106 that illuminates the detector array 114. Alternatively, the detector array 114 may include an energy-resolving detector array such as a multi-layer scintillator/photosensor detector array (FIGS. 3 and 4 below), a direct conversion photon counting detector array with corresponding electronics (FIG. 5), and/or other energy-resolving detector. With a multi-layer scintillator/photosensor detector array, a single or multiple kVps can be used for a multi-energy acquisition. In general, m kVps can be used with n different detector layers for mxn energy acquisitions and energy-dependent detector output signals. With a direct conversion photon counting detector, a single kVp is used to acquire one projection, and spectral information is obtained by pulse height analysis of the electrical output signal of the direct conversion detector.

A volume scan parameter recommender 120 recommends one or more spectral volume scan protocol parameters such as a tube voltage (kVp), tube current (mAs), energy threshold (for photon counting detectors), and/or other spectral scan protocol parameters. The illustrated recommender 120 spectrally decomposes the 2D projections and recommends the parameter based on the spectral decomposition. Generally, for spectral decomposition, data for two different kVps acquired at approximately the same acquisition angle is decomposed into at least two different components, for example, bone and soft tissue. An example spectral decomposition is discussed in Alvarez, R. E. & Macovski, A. "Energy-selective Recon in X-ray Computerized Tomography", Phys Med Biol, 1976, 21, 733-44.

Figure 2:
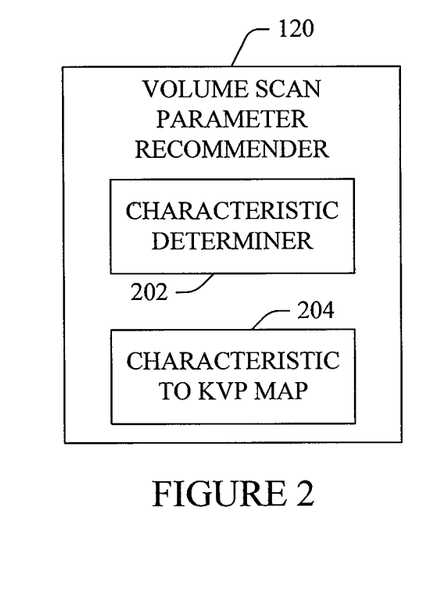
FIG. 2 schematically illustrates an example of the volume scan parameter recommender.

Briefly turning to FIG. 2, a non-limiting example of the recommender 120 is schematically illustrated. A characteristic determiner 202 determines a characteristic of the scanned subject from the decomposed data. For example, based on the decomposition, the recommender 120 can extrapolate an attenuation of the object, even at lower kVp settings. From this data, the recommender 120 can determine whether a volume scan at a particular kVp (e.g., 80 kVp) would suffer from photon starvation. This allows the recommender 120 to recommend a proper kVp value for the volume scan that trades off the risk of photon starvation and a good spectral performance.

In one non-limiting instance, the recommender 120 makes this determination based on a characteristic to kVp map 204, which maps attenuation values (and/or other characteristics) to kVp values and which is based on one or more predetermined tradeoffs between risk of photon starvation and good spectral performance and/or other criteria. For example, the characteristic determiner 202 locates the determined characteristic(s) in the characteristic to kVp map 204 and retrieves a kVp value from the map 204. The map 204 can be generated during a calibration with an appropriate phantom and stored as a look up table (LUT) and/or otherwise. The retrieved kVp value can be automatically loaded in the system 100, displayed for operator review, used to notify the operator that a kVp setting may result in detector overflow or higher patient dose, etc.

By way of non-limiting example, a first 2D projection scan performed at 100 kVp and a second 2D projection scan performed at 140 kVp may be spectrally decomposed to provide data that indicates that the lower kVp setting of a dual-energy scan can be set lower than 100 kVp such as to 80 kVp. Alternatively, the characteristic(s) may indicate that the lower kVp setting should be 100 kVp or greater. Other approaches are also contemplated herein. For example, the recommender 120 may alternatively compute one or more kVp values based on a set of rules, an algorithm, and/or other information.

Generally, the recommender 120 allows for determining and/or optimizing one or more kVps for a spectral volume scan. The volume scan parameter recommender 120 can be implemented via at least one processor executing computer executable instructions embedded or encoded on computer readable storage medium such as physical memory or other non-transitory medium. Additionally or alternatively, the volume scan parameter recommender 120 can be implemented by the at least one processor executing computer executable instructions carried by a carrier wave, signal, or other transitory medium.

Returning to FIG. 1, a general-purpose computer serves as an operator console 122 and includes a human readable output device such as a monitor or display and an input device such as a keyboard and mouse. Software resident on the console 122 allows the operator to interact with the scanner 100 via a graphical user interface (GUI) or otherwise. Such interaction includes selecting two or more 2D projection scans (e.g., a multi-2D projection scan mode), setting and/or modifying scan parameters (e.g., kVp, mAs, etc.) for selected 2D projection scans, selecting a spectral volume scan protocol, setting and/or modifying protocol parameters (e.g., kVps, mAs, etc.) for a selected spectral volume scan.

The interaction may also include visual presentation via the GUI of the recommended parameters (e.g., kVps) and allows for confirmation, modification and/or rejection thereof by the operator of the imaging system 100 using a mouse, touch screen, keyboard, keypad, etc. Alternatively, the recommended parameters may be automatically loaded in the system 100. Alternatively, where the recommended parameters are different from corresponding user selected or default parameters, the console 122 may notify the operator, via visual and/or audible indicator, with a message or warning.

A reconstructor 124 reconstructs the detector array output signal and generates volumetric image data. The reconstructor 124 employs one or more of a conventional, a spectral, an iterative, and/or other reconstruction algorithm. The volumetric image data may include data corresponding to a specific spectral component and/or composite data similar to convention CT image data. The reconstructor 124 can also generate 2D projection images corresponding to a specific spectral component. A subject support 126 such as a couch supports a subject in the examination region 108. The subject support 126 is movable in coordination with scanning so as to guide the subject with respect to the examination region 108 for performing a 2D projection and/or volume scans.

Variations are discussed.

Figure 3:
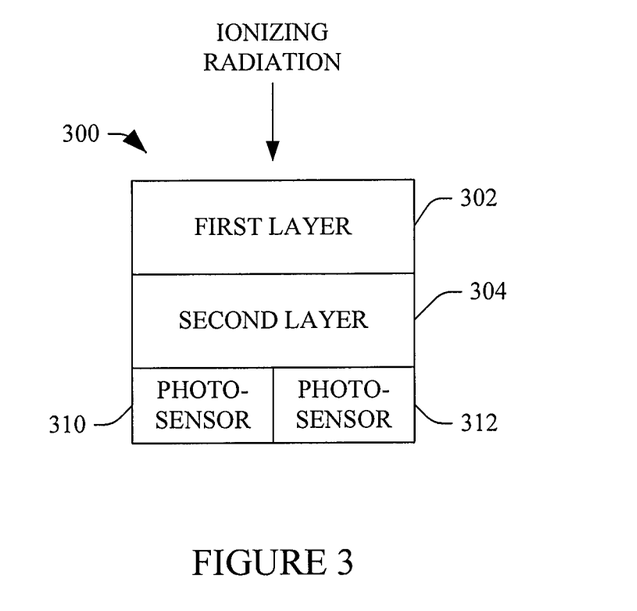
FIG. 3 schematically illustrates a multi-layer scintillator/photosensor based energy-resolving detector.
Figure 4:
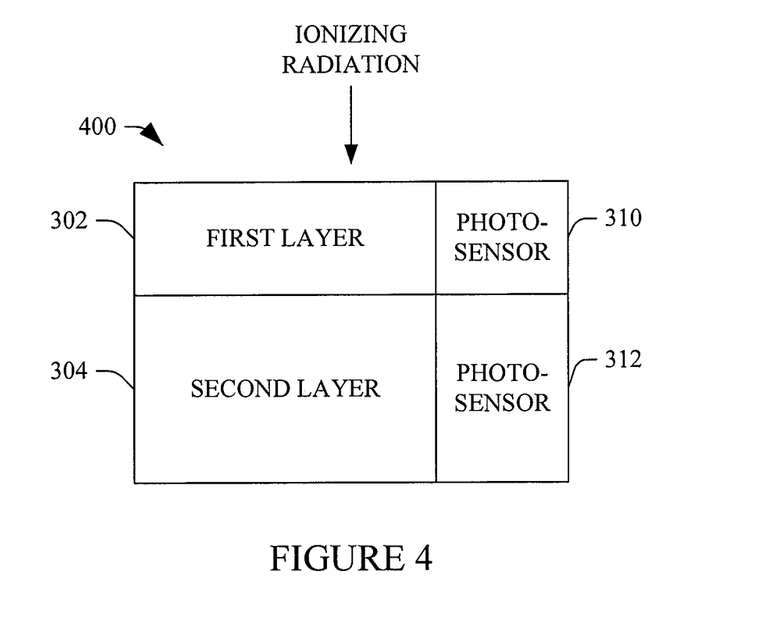
FIG. 4 schematically illustrates another multi-layer scintillator/photosensor based energy-resolving detector.

As briefly noted above, the detector array 114 may alternatively include a multi-layer scintillator/photosensor detector array and/or direct conversion photon counting detector array. FIGS. 3 and 4 schematically show non-limiting examples of two-layer scintillator/photosensor detector arrays 300 and 400, and FIG. 5 show processing electronics for processing the output of a direct conversion photon counting detector array.

In FIG. 3, first and second layers 302 and 304 of scintillation material are coupled such that the first layer 302 is on a side of the detector receiving incoming radiation. Photosensors 310 and 312 are coupled to a second opposing side of the detector 300. Energy absorption, generally, is dependent on thickness. As such, the majority of lower energy photons are absorbed in the first layer 302 and the majority of higher energy photons are absorbed in the second layer 304. The scintillator layers 302 and 304 respectively have emission spectra that match the spectral sensitivities of the photosensors 310 and 312.

As such, substantially only the light emitted by the first layer 302 is absorbed by the photosensor 310, and substantially only the light emitted by the second layer 304 is absorbed by the photosensor 312. The photosensors 310 and 311 output signals indicative of radiation from different energy bands, which correspond to the first and second layers 302 and 304. In FIG. 4, the photosensors 310 and 312 are coupled to a side of the scintillator layers 302 and 304, which is perpendicular to the direction of incoming radiation.

Figure 5:
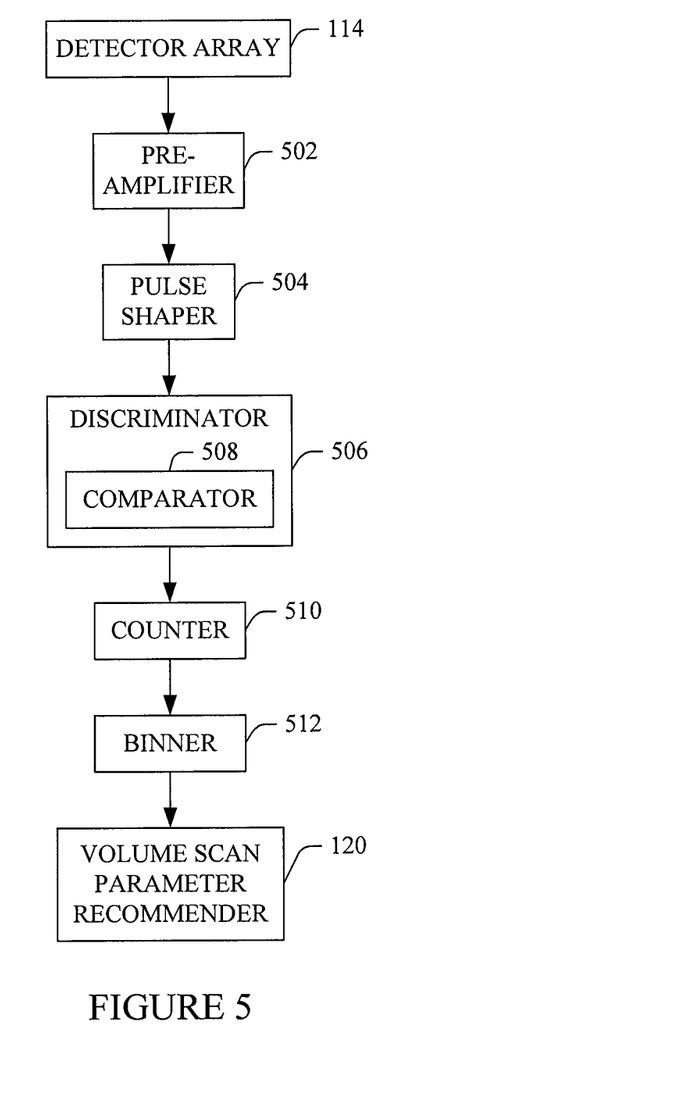
FIG. 5 schematically illustrates direct conversion photon counting detector output processing electronics.

Turning to FIG. 5, the output of the detector array 114 is processed by a pre-amplifier 502, which amplifies the electrical signal output by the detector array 114. A pulse shaper 504 processes the amplified electrical signal and generates a pulse such as voltage or other pulse indicative of the energy of the detected photon. Energy discriminator 506 energy discriminates the pulse. In the illustrated example, the energy discriminator 506 includes a comparator 508, including at least two sub-comparators, which compares the amplitude of the pulse with two or more different energy thresholds that correspond to different energies of interest. The comparator 508 produces an output signal indicative of the energy of the photon based on the comparison.

A counter 510 increments a count value for each threshold based on the output of the energy discriminator 506. For instance, when the output of the comparator 508 for a particular threshold indicates that the amplitude of the pulse exceeds the corresponding threshold, the count value for that threshold is incremented. Energy binner 512 assigns the counted pulses to two or more energy bins based on the counts. Each energy bin encompasses an energy range or window. For example, a bin may be defined for the energy range between two thresholds, where a photon resulting in a count for the lower threshold but not for higher threshold would be assigned to that bin.

The volume scan parameter recommender 120 processes the binned data and the recommender 120 recommends spectral scan parameters such as kVp, mAs, one or more energy thresholds, and/or other parameter(s).

Other variations may include more scintillation layers, and the individual scintillation layers may have equal thickness and/or different thickness. With dual kVps and a dual-layer detector, the recommender 120 recommends settings for four different energy acquisitions. In general, with M kVps and N layers, the recommender 120 recommends settings for MxN different energy acquisitions. With respect to a photon counting detector, with N energy bins, the recommender 120 recommends settings for N different energy acquisitions.

In another variation, the 2D projections can additionally or alternatively be used to determine a filter that improves the spectral performance of a dual layer system. In the case where filter improves the performance only for small patients and degrades the performance for thick patients, the recommender 120 recommendations whether the filter should be used.

In another variation, the imaging system 100 includes more than one source 106. For example, the imaging system 100 may include two sources 106 angularly offset from one another by about ninety degrees along a transverse direction, which is perpendicular to the z-axis, three sources 106 angularly offset from one another by about sixty degrees along the transverse direction, etc. Each of these sources can be operated as described herein to switch between kVps and/or pair with an energy-resolving detector array.

In another variation, the recommender 120 uses the decomposition of the 2D projections to determine a tube current (mAs) for the source 106.

Figure 6:
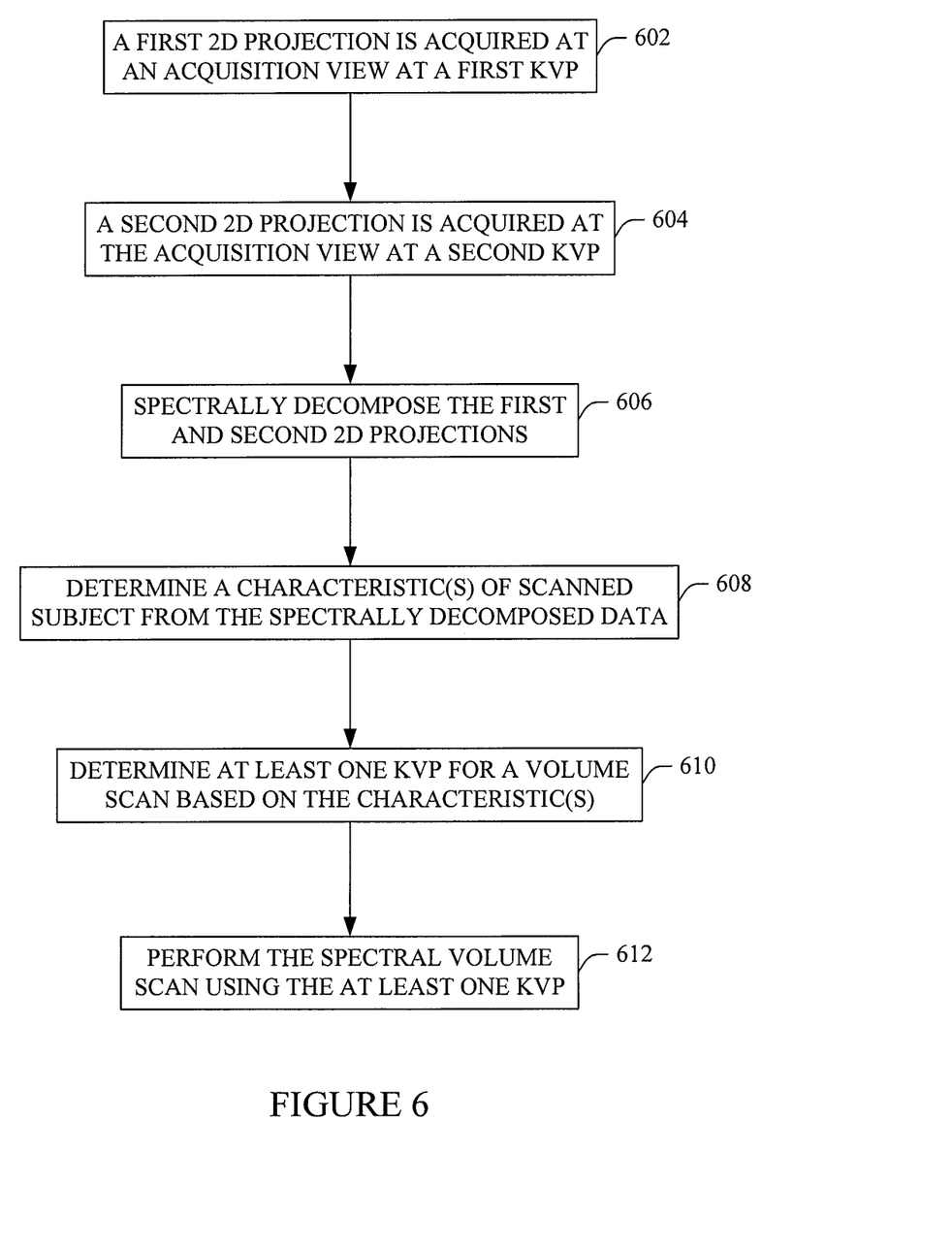
FIG. 6 illustrates an example method for determining a kVp for a spectral volume scan.

In another variation, the recommender 120, for kVp switching, can recommend a kVp cycling parameter. For example, the recommender 120 might recommend how many projections are acquired at each kVp setting. As such, a ratio of data acquired with the two kVp settings can be adjusted in order to satisfy predetermined output criteria. For instance, the criteria may indicate that the data for both kVp settings have the same image quality. Thus, for a thicker patient, the recommender 120 may recommend more projections at the lower kVp setting relative to the higher kVp setting or alternatively longer acquisition periods for the lower kVp settings relative to the higher kVp settings to compensate for poorer statistics. FIG. 6 illustrates an example method.

It is to be appreciated that the ordering of the acts in the methods described herein is not limiting. As such, other orderings are contemplated herein. In addition, one or more acts may be omitted and/or one or more additional acts may be included.

At 602, a first 2D projection is acquired at an acquisition angle using a first kVp.

At 604, a second 2D projection is acquired at the acquisition angle using a second kVp, which is different from the first kVp.

At 606, the first and second 2D projections are spectrally decomposed into at least two components.

At 608, at least one characteristic (e.g., thickness, amount of bone and/or soft tissue, etc.) of the scanned subject is determined from the spectrally decomposed data.

At 610, at least one kVp value for a spectral volume scan of the subject is determined based at least on the determined physical characteristic.

At 612, the determined kVp, along with at least one other determined or user defined kVp, is used to perform the spectral volume scan.

As described herein, the first and second 2D projections may alternatively be obtained with a single kVp and either a multi-layer scintillator/photosensor detector array, direct conversion photon counting detector array, and/or other energy-resolving detector array.

At least a portion of the above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for spectral imaging, comprising:
   receiving a first 2D projection data having a first spectral characteristic, by performing a first 2D projection scan of a subject;
   receiving a second 2D projection data having a second spectral characteristic, by performing a second 2D projection scan of the subject, wherein the first and second spectral characteristics are different;
   spectrally decomposing the first and second 2D projection data into at least two different components;
   determining a physical characteristic of the scanned subject based on the decomposed data;
   recommending at least one kVp value for a volume scan of the subject based on the determined physical characteristic; and
   performing the volume scan of the subject using the recommended at least one kVp value.

2. The method of claim 1, wherein the first spectral characteristic comprises a first kVp value, and the first 2D projection scan of the subject is performed at the first kVp value at a predetermined acquisition angle; and wherein the second spectral characteristic comprises a second kVp value, and the second 2D projection scan of the subject is performed at the second kVp value at the predetermined acquisition angle, wherein the second kVp value is higher than the first kVp value.

3. The method of claim 2, wherein the recommended at least one kVp value is equal to the first kVp.

4. The method of claim 2, wherein the recommended at least one kVp value is less than the first kVp value.

5. The method of claim 1, wherein said performing the volume scan of the subject comprises performing the volume scan of the subject using the recommended at least one kVp value and the second kVp value.

6. The method of claim 1, wherein the first and second 2D projection scans are performed using an array of pixelated detectors, each detector comprising a first photosensor having a first spectral sensitivity and a second photosensor having a second spectral sensitivity that is different from the first spectral sensitivity, wherein said receiving the first 2D projection data comprises receiving the first 2D projection data from an output of the first photosensor, and said receiving the second 2D projection data comprises receiving the second 2D projection data from an output of the second photosensor.

7. The method of claim 1, further comprising:
   visually presenting the recommended at least one kVp value;
   receiving an input signal indicative of a user confirmation of the recommended at least one kVp value; and
   performing the volume scan of the subject using the recommended and user confirmed at least one kVp value.

8. The method of claim 1, further comprising:
   selecting, by a user, a user-selected kVp value for the volume scan;
   determining whether the recommended at least one kVp value is not the same as the user-selected kVp value for the volume scan; and
   visually presenting a warning indicating that the recommended at least one kVp value is not the same as the user-selected kVp value for the volume scan.

9. The method of claim 1, further comprising:
   automatically loading the recommended at least one kVp value in an imaging protocol for the volume scan;
   wherein said performing the volume scan of the subject comprises performing the volume scan of the subject using the recommended and automatically loaded at least one kVp value.

10. The method of claim 1, further comprising:
    recommending at least one mAs value for the volume scan of the subject based on the determined physical characteristic;
    wherein said performing the volume scan of the subject comprises performing the volume scan of the subject using the recommended at least one mAs value.

11. The method of claim 1, further comprising:
    recommending a kVp switching pattern that compensates for poorer photon statistics of the recommended at least one kVp value relative to a second higher kVp value by acquiring more projections with the recommended at least one kVp value;
    wherein said performing the volume scan of the subject comprises performing the volume scan of the subject based on the recommended switching pattern.

12. The method of claim 1, wherein the first 2D projection data corresponds to a first energy bin of photon counting detector electronics and the second 2D projection data corresponds to a second energy bin of the photon counting detector electronics, wherein the method further comprises:
    recommending a mAs value or an energy threshold value for the volume scan of the subject based on the determined physical characteristic, wherein said performing the volume scan of the subject comprises performing the volume scan of the subject based on the recommended mAs value or energy threshold value for the volume scan of the subject.

13. A non-transitory computer-readable medium having one or more executable instructions stored thereon which, when executed by at least one processor, cause the at least one processor to perform a method for spectral imaging, the method comprising:
    receiving a first 2D projection data of a subject having a first spectral characteristic, wherein the first 2D projection data was acquired by an X-ray scanner performing a first 2D projection scan of the subject;
    receiving a second 2D projection data of the subject having a second spectral characteristic, wherein the second 2D projection data was acquired by the X-ray scanner performing a second 2D projection scan of the subject, and wherein the first and second spectral characteristics are different;
    spectrally decomposing the first and second 2D projection data into at least two different components;
    determining a physical characteristic of the scanned subject based on the decomposed data;
    recommending at least one spectral scan parameter value for a volume scan of the subject based on the determined physical characteristic; and controlling the X-ray scanner to perform the volume scan of the subject using the recommended at least one spectral scan parameter value.

\* \* \* \* \*